United States Patent
Grassi (10) Patent No.: US 10,545,516 B2
(45) Date of Patent: Jan. 28, 2020

(54) INDUSTRIAL PROCESS CONTROL TRANSMITTER FOR DETERMINING SOLUTION CONCENTRATION

(71) Applicant: Schneider Electric Systems USA, Inc., Foxboro, MA (US)

(72) Inventor: James H. Grassi, Westwood, MA (US)

(73) Assignee: Schneider Electric Systems USA, Inc., Foxboro, MA (US)

( * ) Notice: Subject to any disclaimer, the term of this patent is extended or adjusted under 35 U.S.C. 154(b) by 199 days.

(21) Appl. No.: 15/667,185

(22) Filed: Aug. 2, 2017

(65) Prior Publication Data
US 2019/0041880 A1    Feb. 7, 2019

(51) Int. Cl.
  *G05D 21/02*    (2006.01)
  *G01N 15/06*    (2006.01)
  *G01N 27/22*    (2006.01)

(52) U.S. Cl.
  CPC ............. *G05D 21/02* (2013.01); *G01N 15/06* (2013.01); *G01N 27/221* (2013.01)

(58) Field of Classification Search
  None
  See application file for complete search history.

(56) References Cited

U.S. PATENT DOCUMENTS

| | | | |
|---|---|---|---|
| 4,458,524 A | 7/1984 | Meador et al. | |
| 2008/0003142 A1* | 1/2008 | Link | B01F 3/0807 422/82.08 |
| 2012/0182030 A1* | 7/2012 | Calciolari | G01N 27/07 324/693 |
| 2013/0285677 A1 | 10/2013 | Hammer | |
| 2015/0160148 A1* | 6/2015 | Stanley | G01N 27/228 324/686 |
| 2015/0226683 A1 | 8/2015 | Feldman et al. | |
| 2016/0077030 A1* | 3/2016 | Stanley | G01N 27/122 324/601 |

OTHER PUBLICATIONS

Extended European Search Report dated Oct. 5, 2018 relating to European Patent Application No. 18184695.7, 13 pages.

\* cited by examiner

*Primary Examiner* — Matthew D Krcha
(74) *Attorney, Agent, or Firm* — Stinson LLP

(57) ABSTRACT

Automated measurement of fluid solution capacitance in industrial processes to determine solution concentration. Industrial process control transmitters determine solution concentration directly from solution capacitance and confirm concentration determinations based on solution conductivity. The industrial process control transmitters include terminals embodied in wire coils and/or metallic plates, at least one processor, and at least one computer readable memory device.

14 Claims, 6 Drawing Sheets

INDUSTRIAL PROCESS CONTROL TRANSMITTER FOR DETERMINING SOLUTION CONCENTRATION

TECHNICAL FIELD

Aspects of the present disclosure generally relate to industrial process devices. More particularly, aspects relate to systems and methods that determine concentration of solutions in industrial processes based on capacitance of the solutions.

BACKGROUND

Industrial processes often involve fluid processing to change or refine raw materials to create end products. The process fluids typically include solutions composed of two or more substances. It is desirable to measure concentration of the substances in the solutions at various points within the process. Known industrial process devices determine solution concentration by measuring conductivity of the solution. Disadvantageously, relying on conductivity measurements is problematic when solution conductivity as a function of concentration is not single-valued. In other words, a single measured solution conductivity value may correspond to more than one solution concentration value. As a result, the measured solution conductivity values can be ambiguous as to which concentration value they correspond.

SUMMARY

Aspects of the disclosure measure capacitance of a solution to determine solution concentration. Solution capacitance as a function of concentration is single-valued, which enables aspects of the disclosure to confirm and eliminate ambiguity in solution concentration determinations based on conductivity. The one-to-one relationship also enables aspects of the disclosure to determine solution concentration from solution capacitance alone.

In an aspect, an industrial process control transmitter includes a drive coil, a response coil, a concentration processor, and a computer readable memory device storing one or more processor-executable instructions. The drive coil is configured to apply an electric field to a fluid process solution. The response coil is configured to sense an inductive response to the applied electric field in the solution. The processor is coupled to the drive and response coils via signal transducers. When executed by the processor, the instructions stored in the memory device cause the processor to implement a method of determining concentration of the fluid process solution. The instructions cause the processor to generate a drive signal in the drive coil to generate the electric field, and measure capacitance of the fluid process solution by monitoring time dependence of the inductive response to the applied electric field. The instructions also cause the processor to determine concentration of the fluid process solution in response to the measured capacitance.

In another aspect, an industrial process control transmitter implements a method of determining concentration of a fluid solution. The transmitter generates a drive signal in an AC circuit, and applies the generated drive signal to a first terminal. Applying the drive signal induces an inductive response in the fluid solution. The transmitter senses the inductive response in the fluid solution at a second terminal. The first terminal, the second terminal, and the fluid solution comprise a capacitor of the AC circuit. The transmitter measures a capacitance of the capacitor by monitoring time dependence of the inductive response to the applied drive signal. The transmitter determines a dielectric constant of the fluid solution based on the measured capacitance. The transmitter also determines concentration of the fluid solution based on the determined dielectric constant.

In yet another aspect, a system includes a drive coil, a response coil, a concentration processor, and a memory device. The drive coil is configured to surround and apply an electric field to a solution in an industrial process. The response coil is configured to surround the solution and sense an inductive response to the applied electric field in the solution. The processor is coupled to the drive and response coils. When executed by the processor, the instructions stored in the memory device cause the processor to implement a method of using solution capacitance to confirm a solution concentration determined by measuring solution conductivity. The executing instructions cause the processor to generate a drive signal in the drive coil to generate the electric field, and receive a response signal from the response coil. The response signal is generated from the inductive response in the solution. The executing instructions also cause the processor to measure conductivity of the solution from the drive and response signals and determine two or more concentration values that correspond to the measured conductivity. Furthermore, the executing instructions cause the processor to measure capacitance of the solution by monitoring a phase difference between the drive signal and the response signal. Based on the measured capacitance, the executing instructions cause the processor to determine a dielectric constant of the solution. Moreover, the executing instructions cause the processor to output one concentration value of the two or more values that most closely matches a concentration of the solution that causes the determined dielectric constant.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1A:
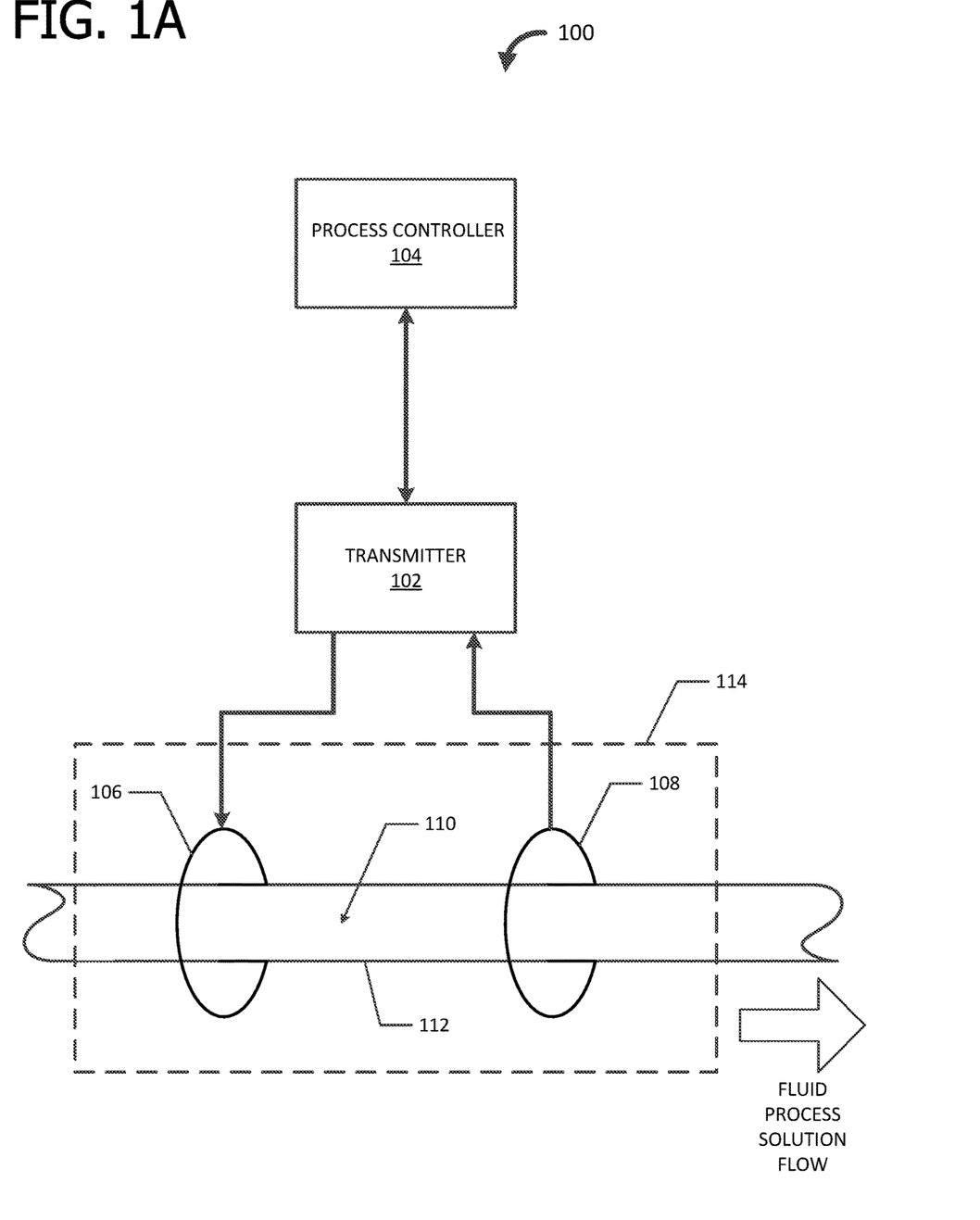
FIGS. 1A and 1B are block diagrams illustrating exemplary systems including a transmitter according to an embodiment.

FIG. 1A is a block diagram of an exemplary embodiment of a system 100. The system 100 includes a transmitter 102, a process controller 104, a first terminal 106, and a second terminal 108. In the exemplary embodiment illustrated in FIG. 1A, the first terminal 106 and the second terminal 108 are metallic wire coils that surround a fluid solution 110 in the process. In accordance with an aspect of the disclosure, this embodiment is utilized in processes in the chemical, oil and gas, food and beverage, and water treatment industries, for example. In an embodiment, the fluid solution 110 is contained within (e.g., flows through, is stagnant within, etc.) a pipe 112. In accordance with an aspect of the disclosure, first terminal 106, second terminal 108, and fluid solution 110 therebetween comprise a capacitor 114, as further described herein.

The transmitter 102 is communicatively coupled to process controller 104 via a communications infrastructure capable of facilitating the exchange of data therebetween. In the embodiment of FIG. 1A, transmitter 102 and process controller 104 are communicatively coupled by a communications infrastructure that supports HART digital signals and/or 4-20 mA analog signals. Communications infrastructures in accordance with aspects of the disclosure include any telecommunications network that facilitates the exchange of data, such as those that operate according to the IEEE 802.3 (e.g., Ethernet) and/or the IEEE 802.11 (e.g., Wi-Fi) protocols, for example. In another embodiment, the communications infrastructure is any medium that allows data to be physically transferred through serial or parallel communication channels (e.g., copper wire, optical fiber, computer bus, wireless communication channel, etc.). The transmitter 102 is electrically and/or communicatively coupled to first terminal 106 and second terminal 108. In an embodiment, transmitter 102 is coupled to each of first terminal 106 and second terminal 108 via one or more signal transducers. For example, a signal transducer coupling transmitter 102 and first terminal 106 may include electronic circuitry that transforms digital signals from transmitter 102 into a drive signal, and a signal transducer coupling transmitter 102 and second terminal 106 may include electronic circuitry that transforms a response signal into a digital signal that can be processed by a computing device (e.g., transmitter 102, an external computer, etc.).

The transmitter 102 is configured to measure capacitance and conductivity of fluid solution 110 for determining concentration of the solution. In an embodiment, transmitter 102 generates an alternating current (AC) voltage (e.g., a drive signal) through first terminal 106 and receives a corresponding AC voltage (e.g., a response signal) from second terminal 108. In accordance with an aspect of the disclosure, transmitter 102 is configured to determine concentration of fluid solution 110 from the measured capacitance alone or from the measured capacitance and the measured conductivity, as further described herein. An exemplary transmitter includes the Model 876EC Intelligent Transmitter available from Schneider Electric.

The first terminal 106 is configured to apply an electric field to fluid solution 110 that corresponds to the drive signal generated by transmitter 102. The electric field brings about an inductive response in fluid solution 110. The second terminal 108 is configured to sense the inductive response and generate a corresponding response signal. In an embodiment, first terminal 106 and second terminal 108 comprise a two-wire loop. In the exemplary embodiment illustrated in FIG. 1A, in which first terminal 106 and second terminal 108 are wire coils, the coils are on the order of centimeters apart and locating the coils closer together provides better capacitance measurements. In accordance with an aspect of the disclosure first terminal 106 and second terminal 108 may be referred to as a sensor. Exemplary sensors that include terminals corresponding to first terminal 106 and second terminal 108 include the FT10 non-invasive, nonmetallic flow-through sensor, the 871EC insertion/submersion sensors, and the 871FT sanitary and industrial flow-through sensors available from Schneider Electric. In an embodiment in which fluid solution 110 flows through pipe 112, transmitter 102 is configured to measure capacitance of the solution regardless of whether second terminal 108 is upstream or downstream of first terminal 106.

In an embodiment, first terminal 106, second terminal 108, and fluid solution 110 therebetween comprise the capacitor 114 (e.g., in a theoretical sense) in the AC circuit formed by transmitter 102, first terminal 106, fluid solution 110, and second terminal 108. Although the analogy between capacitor 114 and a conventional capacitor is not perfect (because the ionic fluid solution 110 is free to move without a mechanical barrier), there are broad similarities. For instance, in capacitor 114 the fluid solution 110 (i.e., a dielectric material) responds to an applied electric field. The time dependent nature of the response in the fluid solution 110 to the applied electric field varies in a consistent manner with the dielectric constant value. Accordingly, monitoring the time dependence of the response voltage (e.g., response signal) to the drive voltage (e.g., drive signal) provides a mechanism to determine which part of a conductance response curve to use, in accordance with an aspect of the disclosure. In an embodiment, monitoring the time dependence includes monitoring the phase angle difference between the drive signal and the response signal. In addition to confirming conductivity measurements, monitoring the time dependent nature of the response signal enables the determination of additional information (e.g., capacitance of fluid solution 110), in accordance with an aspect of the disclosure.

While the conductivity of ionic and other solutions (e.g. fluid solution 110) is not single valued with respect to concentration, the dielectric constant is. The dielectric constant versus concentration of several common salts are given in Levy et al, "Dielectric Constant of Ionic Solutions: A Field-Theory Approach", *Physical Review Letters* 108, 227801 (2012) and Jouyban et al., "A Simple Relationship Between Dielectric Constant of Mixed Solvents with Solvent Composition and Temperature", *International Journal of Pharmaceutics* 269, pgs. 353-360 (2004), each incorporated herein by reference. In addition to the experimental data available therein, one of ordinary skill in the art will understand that the relationship between solution composition and dielectric constant (and thus capacitance) may be developed for any solution through experimentation. The dielectric constant value of a material (e.g., fluid solution 110) affects its capacitance according to Equation 1, which describes a simple parallel plate capacitor (e.g., capacitor 114). In Equation 1, C is capacitance, E is the dielectric constant value, A is plate area, and d is the distance between the plates. In an embodiment, the dielectric constant value is frequency dependent.

$$C = \frac{\varepsilon A}{d} \tag{1}$$

The dielectric constant value E is described by Equation 2. In Equation 2, $E_0$ is the electric field strength without a dielectric material (e.g., fluid solution 110) present (e.g., vacuum≈air, 8.85 e−12 F/m) and E is the electric field strength with the dielectric material present, where $E \leq E_0$ hence $\varepsilon \geq 1$.

$$\varepsilon = \frac{E_0}{E} \tag{2}$$

The introduction of a dielectric material (e.g., fluid solution 110) between electrodes (e.g., first transmitter 106 and second transmitter 108) affects the capacitance according to Equation 3. As $\varepsilon \geq 1$ in Equation 3, the capacitance increases with the introduction of a dielectric material (e.g., fluid solution 110).

$$C = \varepsilon C_0 \quad (3)$$

For two capacitors with the same resistance, but different capacitance, the observed voltage during discharge will vary as a function of time, as described by Equation 4. The larger the capacitance, the longer the discharge. In Equation 4, V is the observed voltage, $V_0$ is the charged voltage, t is time, R is resistance, and C is capacitance.

$$V = V_0 e^{-t/RC} \quad (4)$$

The transmitter 102 is configured to measure capacitance via one or more methods, in accordance with the relationships described by Equation 5.

$$i = C \frac{dV}{dt} \quad (5)$$

One method includes maintaining a known current (i) and measuring the change in voltage (dV/dt) across the capacitor (e.g., capacitor 114) (i.e., the change in voltage required to maintain the current) and deduce the capacitance. Another method includes applying a pulsed voltage train to the system. When the voltage is applied, the capacitor (e.g., capacitor 114) begins to charge and the voltage across the capacitor increases. The measured voltage across the capacitor is compared to a threshold value (e.g., stored in a memory device) that is used to end the voltage pulse. The duration of the voltage pulse is then compared to the RC time constant of the circuit where resistance (R) is known and capacitance (C) is determined.

Yet another method includes monitoring the reactance of the system. A simple resistor is indifferent to an AC voltage while the effective resistance of a capacitor is affected by the frequency in accordance with Equation 6. In Equation 6, $X_C$ is the capacitor reactance in Ohms, f is the signal frequency in Hertz, and C is the capacitance in Farads.

$$X_C = \frac{1}{2\pi f c} \quad (6)$$

A real system includes some fixed resistance in series with the capacitance of fluid solution 110, the phase angle between the voltage and current can be utilized to glean information about the system. The phase angle is described by Equation 7. In Equation 7, Z is the observed impedance (V/I) in Ohms, R is the fixed resistance in Ohms, and $X_C$ is the cell reactance in Ohms.

$$\tan(\theta) = \frac{X_C}{R} \quad (7)$$

Because Z and θ can be measured, $X_C$ and subsequently the solution capacitance can be determined. In addition, because R is not a function of frequency, but $X_C$ is, taking measurements at multiple frequencies enables an alternative (e.g., confirmative) method as the use of multiple frequencies permits isolating each term and determining the reactance of fluid solution 110 and hence the capacitance of fluid solution 110. In an embodiment, transmitter 102 functions as a dielectric spectrometer.

Figure 1B:
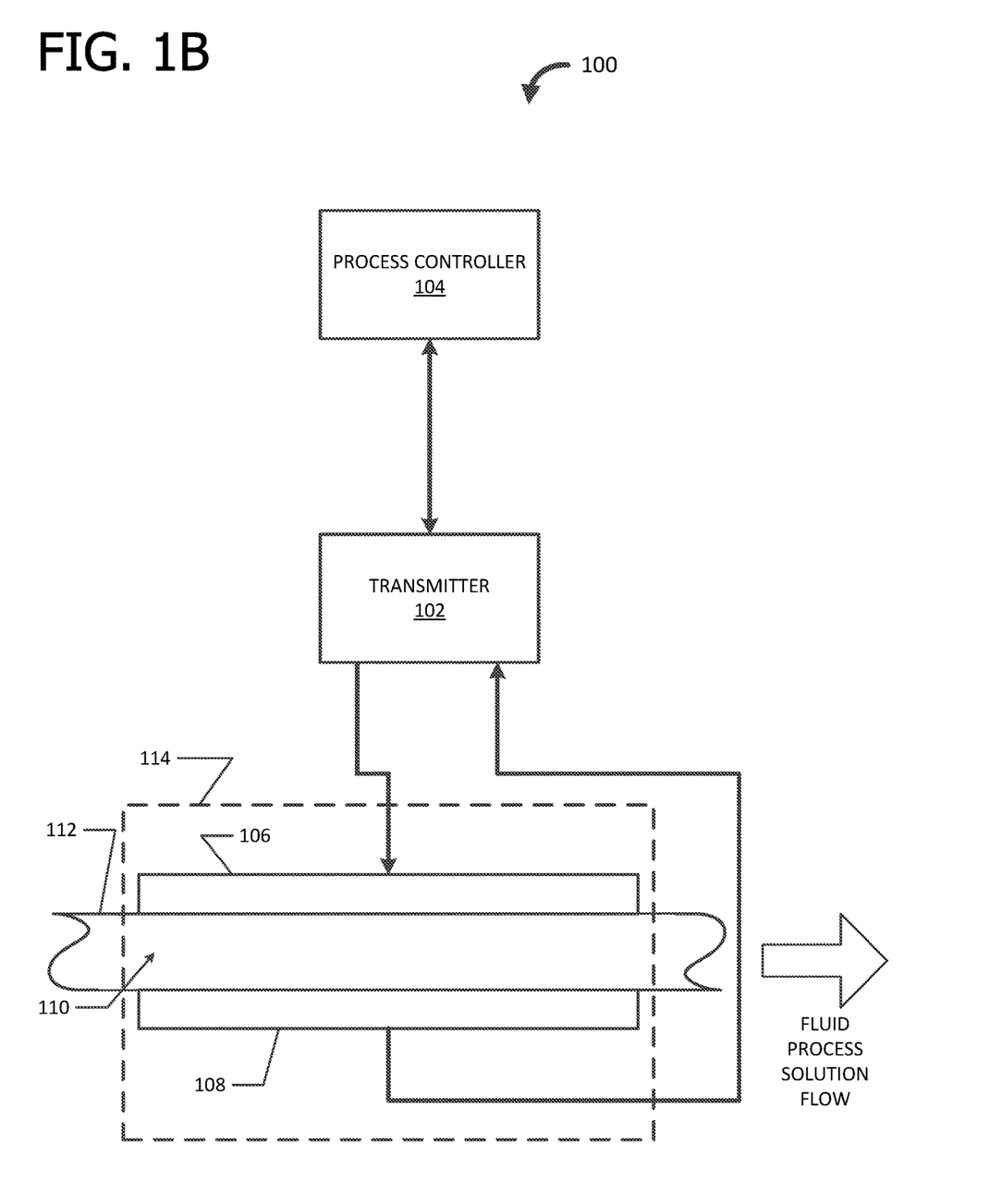

FIG. 1B is a block diagram of another exemplary embodiment of system 100. In this exemplary embodiment, first terminal 106 and second terminal 108 are flat metallic plates that surround fluid solution 110 in the process. In accordance with an aspect of the disclosure, this embodiment is utilized in processes in the medical and pharmaceutical industries, for example. Although FIGS. 1A and 1B illustrate a direction of flow of fluid solution 110 through pipe 112, one of ordinary skill in the art will understand that fluid solution 110 may flow in the opposite direction or may not flow at all (i.e., be stagnant) in accordance with one or more aspects of the disclosure.

Figure 2:
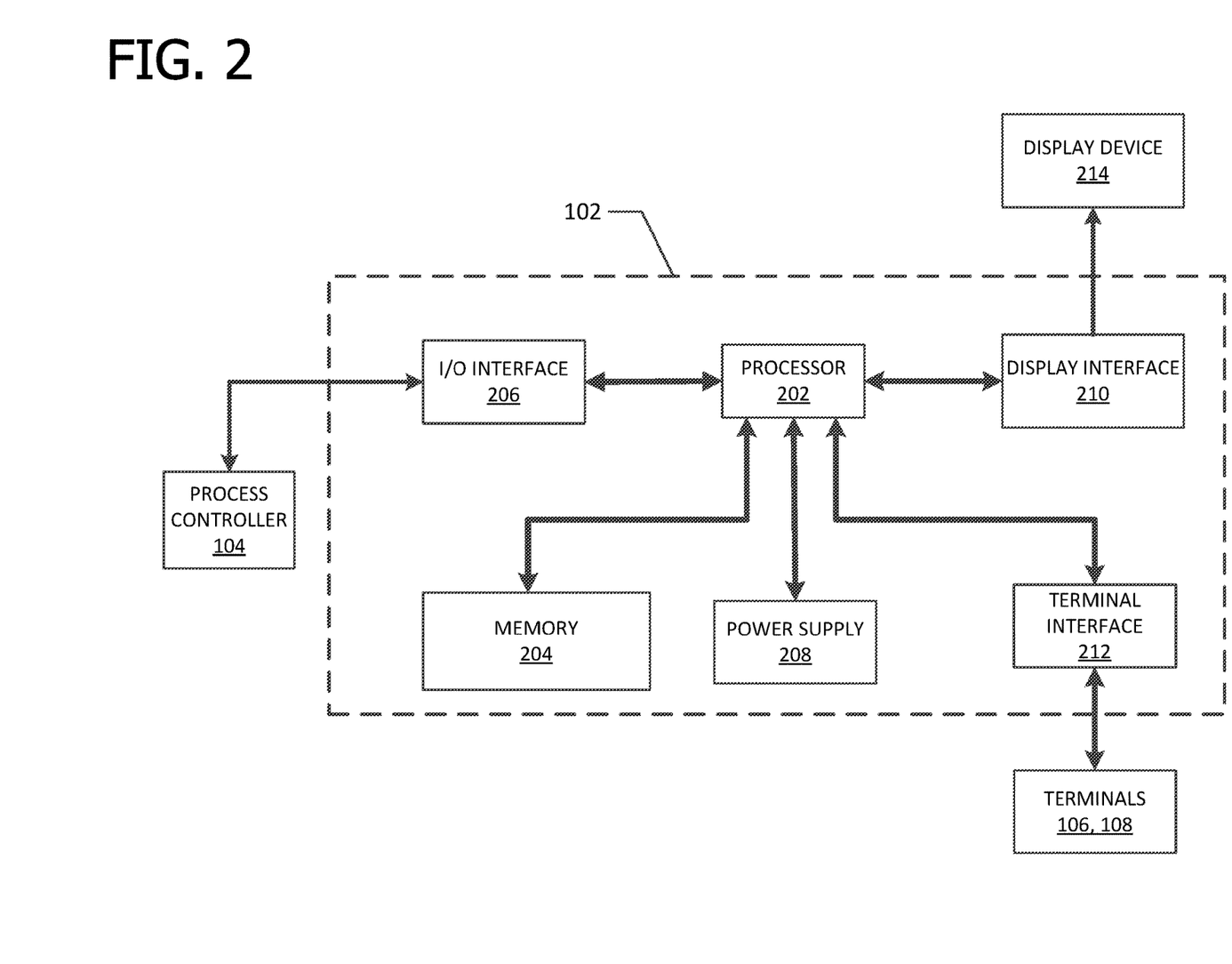
FIG. 2 is a block diagram illustrating the transmitter of FIGS. 1A and 1B.

FIG. 2 illustrates an exemplary architecture of transmitter 102 configured to provide aspects of the systems and processes described herein via a software environment. In this embodiment, transmitter 102 includes a concentration processor 202, a memory device 204, an input/output (I/O) interface 206, a power supply 208, a display interface 210, and a terminal interface 212. The memory 204 includes processor-executable instructions for executing by processor 202 that carry out processes for measuring conductivity and/or capacitance of fluid solution 110 and determining concentration of solution 110, as further described herein. In this manner, transmitter 102 comprises a special-purpose computing device for determining solution capacitance and concentration and generating a graphical display indicating the capacitance and concentration on display device 214 in accordance with an aspect of the disclosure.

The processor 202, memory 204, I/O interface 206, power supply 208, display interface 210, and terminal interface 212 are communicatively connected and/or electrically connected to each other. The I/O interface 206 is communicatively connected to process controller 104, as further described herein. The processor 202 is adapted to execute processor-executable instructions stored in the memory 204 for measuring conductivity and/or capacitance of fluid solution 110 and determining concentration of fluid solution 110 from the measurements in real time. The I/O interface 206 of FIG. 2 provides a physical data connection between transmitter 102 and process controller 104. In an embodiment, I/O interface 206 is a network interface card (NIC) or modem. The display interface 210 provides a physical data connection between transmitter 102 and display device 214. In an embodiment, display device 214 is an LCD indicator display that includes a keypad for human interface. In another embodiment, display device 214 is a touchscreen on transmitter 102 and/or a touchscreen of a smartphone, tablet computing device, or the like. The terminal interface 212 provides an electrical connection between transmitter 102 and first terminal 106 and second terminal 108.

Figure 3:
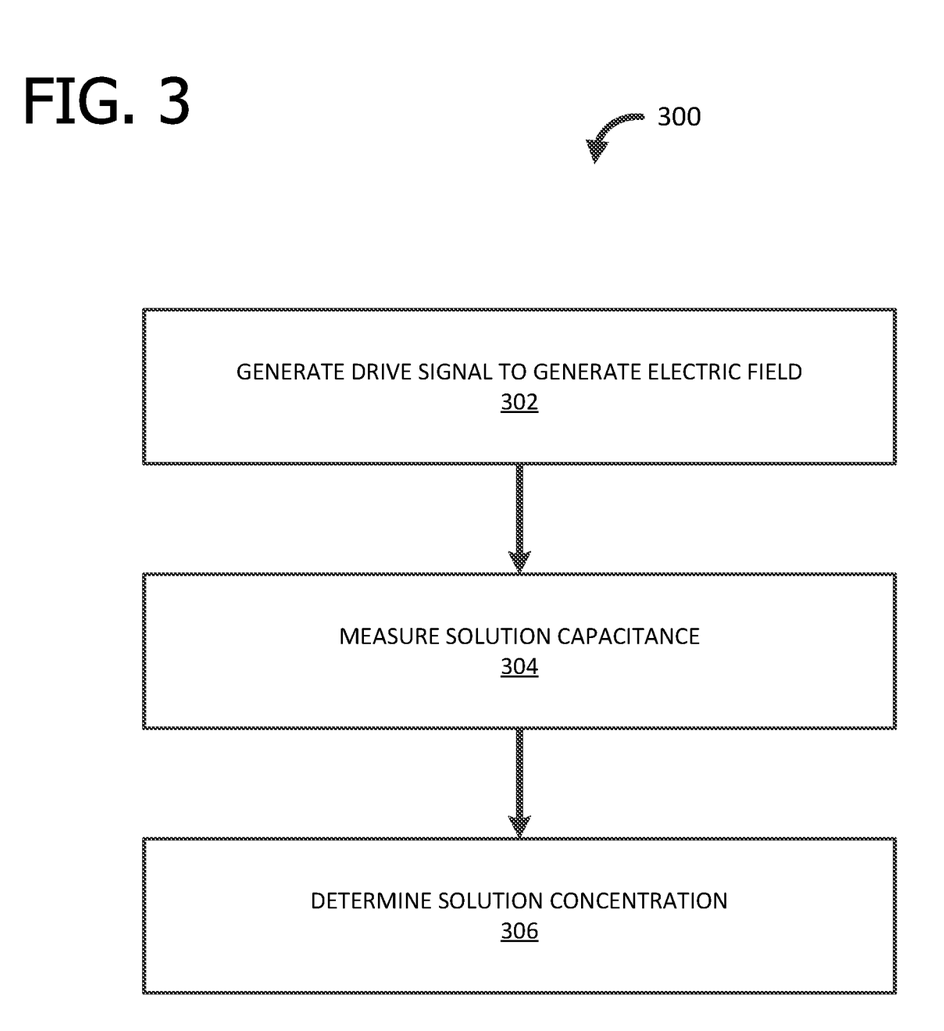
FIGS. 3-5 are block diagrams illustrating exemplary methods of determining solution concentration from solution capacitance according to an embodiment.

FIG. 3 illustrates an exemplary method 300 of determining concentration of fluid solution 110. In the method 300, transmitter 102 generates (302) a drive signal in first terminal 106 (e.g., a drive coil, a drive plate, etc.) to generate an electric field in fluid solution 110. The electric field brings about an inductive response in fluid solution 110. The transmitter 102 measures (304) the capacitance of fluid solution 110 by monitoring the time dependence of the inductive response via second terminal 108 (e.g., a response coil). In an embodiment, transmitter 102 utilizes at least one of the three methods further described herein for measuring capacitance from the applied electric field. The transmitter 102 also determines (306) concentration of the fluid solution 110 from the measured capacitance.

Figure 4:
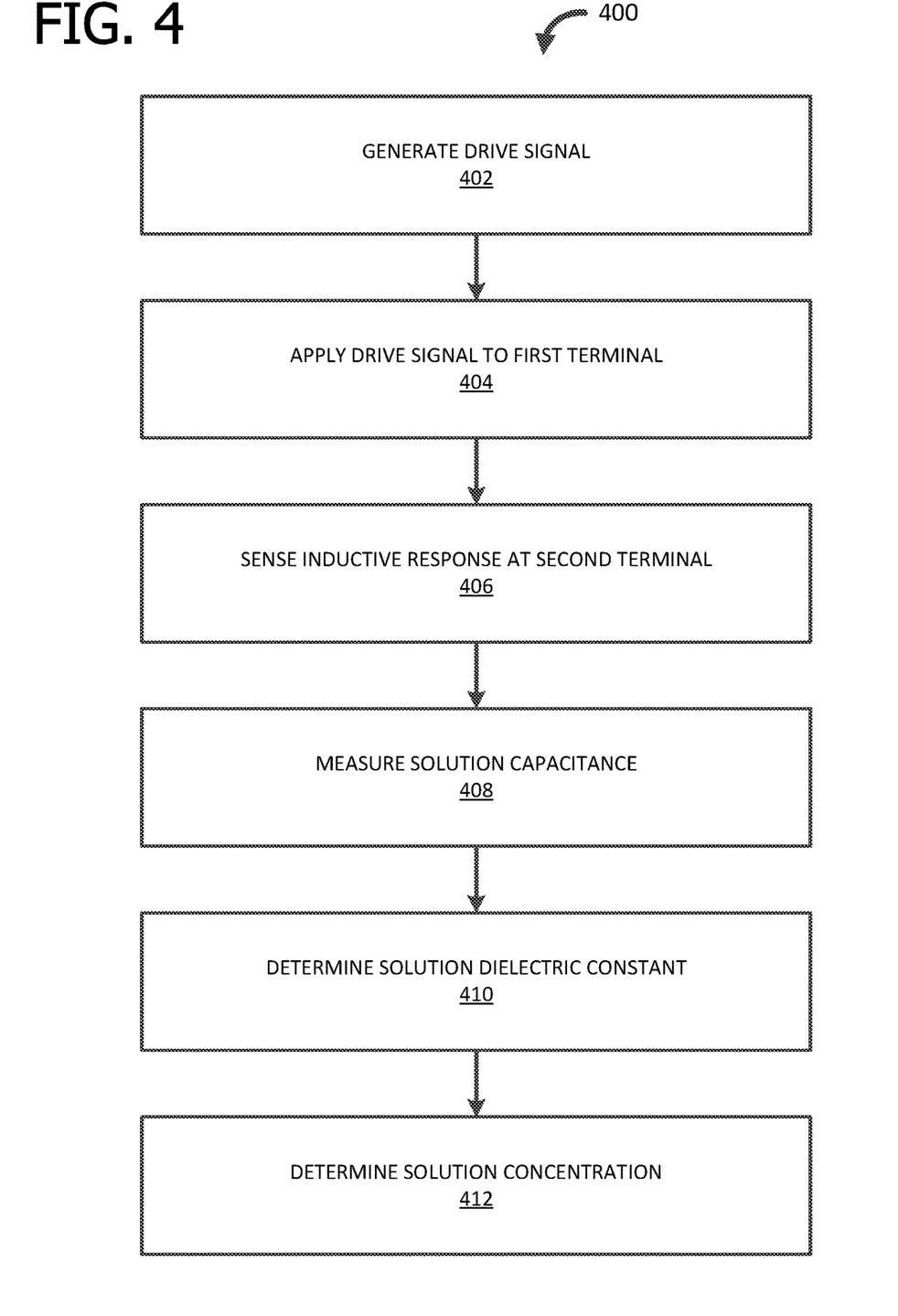

FIG. 4 illustrates another exemplary method 400 of determining concentration of fluid solution 110. In the method 400, transmitter 102 generates (402) a drive signal and applies (404) the drive signal to first terminal 106. Applying the drive signal induces an inductive response in fluid solution 110. The transmitter 102 senses (406) the inductive response in the fluid solution 110 at second terminal 108. The transmitter 102 measures (408) the capacitance of fluid solution 110 by monitoring the time dependence of the inductive response to the applied drive signal. In an embodiment, transmitter 102 monitors the reactance, as further described herein. The transmitter 102 determines (410) the dielectric constant value of the fluid solution 110 based on the measured capacitance. In an embodiment, transmitter 102 executes software instructions for utilizing Equations 1, 2, 3, and/or 4 to determine the dielectric constant value of the fluid solution 110 based on the measured capacitance. The transmitter 102 also determines (412) the concentration of fluid solution 110 based on the determined dielectric constant value. In an embodiment, transmitter 102 utilizes a capacitance response curve stored in a memory device of the transmitter (e.g., memory device 204) to determine the concentration from the dielectric constant value.

Figure 5:
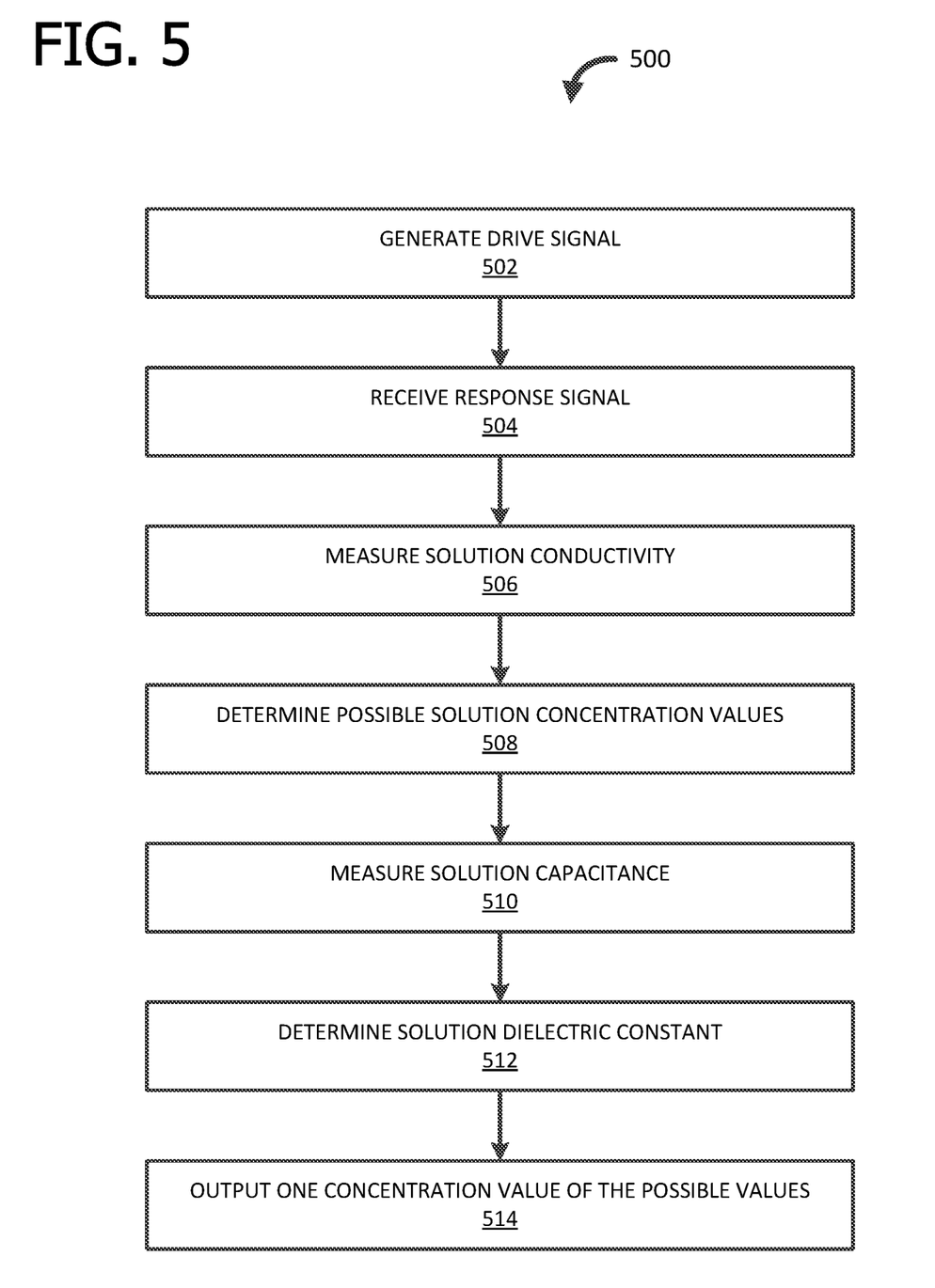

FIG. 5 illustrates an exemplary method 500 of using solution capacitance to confirm a solution concentration determined by measuring solution conductivity. In the method 500, transmitter 102 generates (502) a drive signal in first terminal 106 to generate an electric field in fluid solution 110. The electric field brings about an inductive response in fluid solution 110. The transmitter 102 receives (504) a response signal from second terminal 108. The transmitter 102 measures (506) conductivity of fluid solution 110 based on the drive signal and the response signal. Based on the measured conductivity, transmitter 102 determines (508) two or more concentration values that correspond to the measured conductivity. The measured conductivity corresponds to two or more possible concentration values because solution conductivity as a function of concentration is not single-valued. The transmitter 102 then measures (510) the capacitance of fluid solution 110 by monitoring a phase difference between the drive signal and the response signal. Based on the measured capacitance, transmitter 102 determines (512) a dielectric constant value of fluid solution 110. In an embodiment, transmitter 102 executes software instructions for utilizing Equations 1, 2, 3, and/or 4 to determine the dielectric constant value of the fluid solution 110 based on the measured capacitance. The transmitter 102 outputs (514) only a single concentration value of the two or more possible concentration values of fluid solution 110. The transmitter 102 selects the outputted concentration value based on which possible concentration value most closely matches a concentration of fluid solution 110 that causes the determined dielectric constant value of fluid solution 110. In other words, the dielectric constant (and thus the capacitance) of fluid solution 110 varies according to the concentration in a one-to-one manner such that the determined dielectric constant corresponds to one, and only one, of the possible concentration values. In an embodiment, transmitter 102 outputs the single concentration value via a display device (e.g., display device 214). In another embodiment, transmitter 102 outputs the single concentration value to process controller 104 (e.g., via I/O interface 206 and the communications infrastructure).

In an embodiment, industrial process control transmitter 102 includes a drive coil (e.g., first terminal 106), a response coil (e.g., second terminal 108), processor 202, and memory device 204 storing one or more processor-executable instructions. The drive coil is configured to surround and apply an electric field to fluid solution 110 in an industrial process. The drive coil comprises a first terminal (e.g., first terminal 106) of capacitor 114. The response coil is configured to surround fluid solution 110 and sense an inductive response to the applied electric field in the solution. The response coil comprises a second terminal (e.g., second terminal 108) of capacitor 114, and fluid solution 110 between the coils comprises a dielectric of capacitor 114. The processor 202 is coupled to the drive and response coils (e.g., via terminal interface 212). When executed by processor 202, the instructions stored in memory device 204 cause processor 202 to implement a method of determining concentration of fluid solution 110. The instructions cause processor 202 to generate (e.g., step 302) a drive signal in the drive coil to generate the electric field and measure (e.g., step 304) capacitance of fluid solution 110 by monitoring time dependence of the inductive response to the applied electric field. The instructions also cause processor 202 to determine (e.g., step 306) concentration of the fluid process solution from the measured capacitance. One of ordinary skill in the art will understand that the drive and response coils may additionally or alternatively be immersed in the solution and/or form at least a portion of a pipe (e.g., pipe 112) within which fluid solution 110 is contained.

In another embodiment, transmitter 102 implements a method of determining concentration of fluid solution 110. The transmitter 102 generates (e.g., step 402) a drive signal in an AC circuit, and applies (e.g., step 404) the generated drive signal to first terminal 106. Applying the drive signal induces an inductive response in fluid solution 110. The transmitter 102 senses (e.g., step 406) the inductive response in fluid solution 110 at second terminal 108. The first terminal 106, second terminal 108, and fluid solution 110 comprise capacitor 114. The transmitter 102 measures (e.g., step 408) a capacitance of capacitor 114 by monitoring time dependence of the inductive response to the applied drive signal. The transmitter 102 determines (e.g., step 410) a dielectric constant of fluid solution 110 based on the measured capacitance. The transmitter 102 also determines (e.g., step 412) concentration of fluid solution 110 based on the determined dielectric constant.

In yet another embodiment, a system in accordance with an aspect of the disclosure includes a drive coil (e.g., first terminal 106), a response coil (e.g., second terminal 108), processor 202, and memory device 204. The drive coil is configured to surround and apply an electric field to fluid solution 110 in an industrial process. The drive coil comprises a first terminal (e.g., first terminal 106) of capacitor 114. The response coil is configured to surround fluid solution 110 and sense an inductive response to the applied electric field in the solution. The response coil comprises a second terminal (e.g., second terminal 108) of capacitor 114, and fluid solution 110 between the coils comprises a dielectric of capacitor 114. The processor 202 is coupled to the drive and response coils (e.g., via terminal interface 212). When executed by processor 202, the instructions stored in memory device 204 cause processor 202 to implement a method of using solution capacitance to confirm a solution concentration determined by measuring solution conductivity. The executing instructions cause processor 202 to generate (e.g., step 502) a drive signal in the drive coil to generate the electric field, and receive (e.g., step 504) a response signal from the response coil. The response signal is generated from the inductive response in fluid solution 110. The executing instructions also cause processor 202 to measure (e.g., step 506) conductivity of fluid solution 110 from the drive signal and the response signal and determine (e.g., step 508) two or more concentration values that correspond to the measured conductivity. Furthermore, the executing instructions cause processor 202 to measure (e.g., step 510) capacitance of fluid solution 110 by monitoring a phase difference between the drive signal and the response signal. Based on the measured capacitance, the executing instructions cause processor 202 to determine a dielectric constant of fluid solution 110. Moreover, the executing instructions cause processor 202 to output one concentration value of the two or more values that most closely matches a concentration of fluid solution 110 that causes the determined dielectric constant.

In addition to the embodiments described above, embodiments of the present disclosure may comprise a special purpose computer including a variety of computer hardware, as described in greater detail below.

Embodiments within the scope of the present disclosure also include computer-readable media for carrying or having computer-executable instructions or data structures stored thereon. Such computer-readable media can be any available media that can be accessed by a special purpose computer. By way of example, and not limitation, computer-readable storage media include both volatile and nonvolatile, removable and non-removable media implemented in any method or technology for storage of information such as computer readable instructions, data structures, program modules or other data. Computer storage media are non-transitory and include, but are not limited to, random access memory (RAM), read only memory (ROM), electrically erasable programmable ROM (EEPROM), compact disk ROM (CD-ROM), digital versatile disks (DVD), or other optical disk storage, solid state drives (SSDs), magnetic cassettes, magnetic tape, magnetic disk storage, or other magnetic storage devices, or any other medium that can be used to carry or store desired program code means in the form of computer-executable instructions or data structures and that can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which aspects of the disclosure may be implemented. Although not required, aspects of the disclosure will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that aspects of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Aspects of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing aspects of the disclosure includes a special purpose computing device in the form of a conventional computer, including a processing unit, a system memory, and a system bus that couples various system components including the system memory to the processing unit. The system bus may be any of several types of bus structures including a memory bus or memory controller, a peripheral bus, and a local bus using any of a variety of bus architectures. The system memory includes nonvolatile and volatile memory types. A basic input/output system (BIOS), containing the basic routines that help transfer information between elements within the computer, such as during start-up, may be stored in ROM. Further, the computer may include any device (e.g., computer, laptop, tablet, PDA, cell phone, mobile phone, a smart television, and the like) that is capable of receiving or transmitting an IP address wirelessly to or from the internet.

The computer may also include a magnetic hard disk drive for reading from and writing to a magnetic hard disk, a magnetic disk drive for reading from or writing to a removable magnetic disk, and an optical disk drive for reading from or writing to removable optical disk such as a CD-ROM or other optical media. The magnetic hard disk drive, magnetic disk drive, and optical disk drive are connected to the system bus by a hard disk drive interface, a magnetic disk drive-interface, and an optical drive interface, respectively. The drives and their associated computer-readable media provide nonvolatile storage of computer-executable instructions, data structures, program modules, and other data for the computer. Although the exemplary environment described herein employs a magnetic hard disk, a removable magnetic disk, and a removable optical disk, other types of computer readable media for storing data can be used, including magnetic cassettes, flash memory cards, digital video disks, Bernoulli cartridges, RAMs, ROMs, SSDs, and the like.

Communication media typically embody computer readable instructions, data structures, program modules or other data in a modulated data signal such as a carrier wave or other transport mechanism and includes any information delivery media.

One or more aspects of the disclosure may be embodied in computer-executable instructions (i.e., software), routines, or functions stored in system memory or nonvolatile memory as application programs, program modules, and/or program data. The software may alternatively be stored remotely, such as on a remote computer with remote application programs. Generally, program modules include routines, programs, objects, components, data structures, etc. that perform particular tasks or implement particular abstract data types when executed by a processor in a computer or other device. The computer executable instructions may be stored on one or more tangible, non-transitory computer readable media (e.g., hard disk, optical disk, removable storage media, solid state memory, RAM, etc.) and executed by one or more processors or other devices. As will be appreciated by one of skill in the art, the functionality of the program modules may be combined or distributed as desired in various embodiments. In addition, the functionality may be embodied in whole or in part in firmware or hardware equivalents such as integrated circuits, application specific integrated circuits, field programmable gate arrays (FPGA), and the like.

The computer may operate in a networked environment using logical connections to one or more remote computers. The remote computers may each be another personal computer, a tablet, a PDA, a server, a router, a network PC, a peer device, or other common network node, and typically include many or all of the elements described above relative to the computer. The logical connections include a local area network (LAN) and a wide area network (WAN) that are presented here by way of example and not limitation. Such networking environments are commonplace in office-wide or enterprise-wide computer networks, intranets and the Internet.

When used in a LAN networking environment, the computer is connected to the local network through a network interface or adapter. When used in a WAN networking environment, the computer may include a modem, a wireless link, or other means for establishing communications over the wide area network, such as the Internet. The modem, which may be internal or external, is connected to the system bus via the serial port interface. In a networked environment, program modules depicted relative to the computer, or portions thereof, may be stored in the remote memory storage device. It will be appreciated that the network connections shown are exemplary and other means of establishing communications over wide area network may be used.

Preferably, computer-executable instructions are stored in a memory, such as the hard disk drive, and executed by the computer. Advantageously, the computer processor has the capability to perform all operations (e.g., execute computer-executable instructions) in real-time.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the disclosure.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. An industrial process control transmitter, comprising:
a drive coil configured to apply an electric field to a fluid process solution contained within a pipe of an industrial process;
a response coil configured to sense an inductive response to the applied electric field in the fluid process solution;
a concentration processor coupled to the drive coil and the response coil via signal transducers; and
a non-transitory computer-readable memory device coupled to the processor and storing one or more processor-executable instructions thereon, said processor-executable instructions, when executed by the processor, cause the processor to:
generate a drive signal in the drive coil to generate the electric field,
receive a response signal from the response coil, said response signal generated from the inductive response in the fluid process solution,
measure a conductivity of the fluid process solution from the drive signal and the response signal, wherein the conductivity corresponds to a plurality of concentrations of the fluid process solution,
measure capacitance of the fluid process solution by monitoring time dependence of the inductive response to the applied electric field,
determine a dielectric constant of the fluid process solution based on the measured capacitance, and
determine which of the plurality of concentrations is more accurate based on a concentration of the fluid process solution that causes the determined dielectric constant.

2. The industrial process control transmitter of claim 1, wherein the response coil and the drive coil are one of:
configured to surround the pipe and the fluid process solution within the pipe,
configured to comprise at least a portion of the pipe and surround the fluid process solution therewithin, and
configured to be immersed in the fluid process solution within the pipe.

3. The industrial process control transmitter of claim 1, wherein the drive coil comprises a first terminal of a capacitor, the response coil comprises a second terminal of the capacitor, and the fluid process solution therebetween comprises a dielectric material of the capacitor.

4. The industrial process control transmitter of claim 3, wherein measuring the capacitance of the fluid process solution by monitoring time dependence of the inductive response comprises:
measuring an impedance of the capacitor;
measuring a phase angle between a voltage and a current of the drive signal;
determining a reactance of the capacitor based on the measured impedance, the measured phase angle, and a fixed resistance of the capacitor; and
determining the capacitance of the fluid process solution based on the determined reactance and a frequency of the drive signal.

5. The industrial process control transmitter of claim 3, wherein the applied electric field comprises a pulsed voltage train, and wherein measuring the capacitance of the fluid process solution by monitoring time dependence of the inductive response comprises:

ending the pulsed voltage train when the voltage across the capacitor is equal to or greater than a predetermined threshold value, and determining the capacitance of the fluid process solution by comparing duration of the pulsed voltage train to an RC time constant of the capacitor.

6. The industrial process control transmitter of claim 3, wherein the first terminal and the second terminal each comprise a wire coil, and wherein the wire coils are one of:
configured to surround a pipe through which the fluid solution flows,
configured to comprise at least in part the pipe through which the fluid solution flows, and
configured to be immersed in the fluid solution within the pipe.

7. The industrial process control transmitter of claim 3, wherein the first terminal and the second terminal each comprise a metallic plate, wherein the metallic plates are separated by the fluid process solution.

8. The industrial process control transmitter of claim 1, wherein measuring the capacitance of the fluid process solution by monitoring time dependence of the inductive response comprises measuring a change in voltage in the response coil required to maintain a known current in the drive coil.

9. The industrial process control transmitter of claim 1, wherein the processor-executable instructions, when executed by the processor, further cause the processor to confirm another determined concentration of the fluid process solution based on conductivity thereof by comparing the determined concentration of the fluid process solution from the determined capacitance to the another determined concentration.

10. The industrial process control transmitter of claim 1, wherein the processor-executable instructions, when executed by the processor, further cause the processor to determine a dielectric constant of the fluid solution based on the measured capacitance and to determine the concentration of the fluid solution based on the determined dielectric constant thereof.

11. The industrial process control transmitter of claim 10, wherein determining the concentration of the fluid process solution comprises determining a concentration value that corresponds to the determined dielectric constant along a curve representing dielectric constant values as a function of concentration values, said curve specific to the fluid process solution.

12. The industrial process control transmitter of claim 10, wherein the processor-executable instructions, when executed by the processor, further cause the processor to confirm a second determined concentration of the fluid process solution based on conductivity thereof by comparing the determined concentration of the fluid process solution from the determined dielectric constant to the second determined concentration.

13. The industrial process control transmitter of claim 12, further comprising a display device and wherein the processor-executable instructions, when executed by the processor, further cause the processor to output the confirmed second concentration of the fluid solution to the display device.

14. The industrial process control transmitter of claim 1, wherein the processor-executable instructions, when executed by the processor, further cause the processor to generate an output value representing the determined concentration.

* * * * *